(12) United States Patent
Webster

(10) Patent No.: US 12,329,414 B2
(45) Date of Patent: Jun. 17, 2025

(54) ACNE EXTRACTOR FOR TREATING SUPERFICIAL ACNE

(71) Applicant: SKIN SAFEGUARD INCORPORATED, Salem, OR (US)

(72) Inventor: Noah Webster, San Diego, CA (US)

(73) Assignee: Skin Safeguard Incorporated, Salem, OR (US)

( * ) Notice: Subject to any disclaimer, the term of this patent is extended or adjusted under 35 U.S.C. 154(b) by 244 days.

(21) Appl. No.: 17/890,096

(22) Filed: Aug. 17, 2022

(65) Prior Publication Data

US 2023/0053796 A1 Feb. 23, 2023

Related U.S. Application Data

(60) Provisional application No. 63/234,167, filed on Aug. 17, 2021.

(51) Int. Cl.
*A61B 17/50* (2006.01)
*A61B 17/00* (2006.01)

(52) U.S. Cl.
CPC .... *A61B 17/50* (2013.01); *A61B 2017/00747* (2013.01); *A61B 2017/00862* (2013.01)

(58) Field of Classification Search
CPC .......... A61B 17/50; A61B 2017/00747; A61B 2017/00862; A61B 17/3209; A61B 2017/00473; A61B 2017/00858; A61B 2090/065
See application file for complete search history.

(56) References Cited

U.S. PATENT DOCUMENTS

| | | | | |
|---|---|---|---|---|
| 834,683 A * | 10/1906 | Severin | ............ | A61B 17/32 606/211 |
| 896,338 A * | 8/1908 | Tolman | ............ | A61F 11/006 294/99.2 |
| 906,085 A * | 12/1908 | Tolman | ............ | A61B 17/32 132/73 |
| D279,405 S * | 6/1985 | Lentz | ............ | D24/133 |
| 4,681,101 A * | 7/1987 | Bicoll | ............ | A61H 39/04 606/185 |
| 5,395,380 A * | 3/1995 | Berkovich | ............ | A61B 17/54 604/290 |
| 5,431,665 A * | 7/1995 | Li | ............ | A61B 17/1285 606/139 |
| 5,649,942 A * | 7/1997 | Yeh | ............ | A61B 17/50 606/162 |

(Continued)

FOREIGN PATENT DOCUMENTS

WO WO-2008097043 A1 * 8/2008 ............ A61B 17/50

*Primary Examiner* — Julian W Woo
(74) *Attorney, Agent, or Firm* — Mintz Levin Cohn Ferris Glovsky and Popeo, P.C.

(57) ABSTRACT

Methods, devices, and systems are described for an acne extractor for treating superficial acne. The acne extractor includes a curved elongated handle having a distal end. A head is coupled to the distal end of the curved elongated handle. The head extends from curved elongated handle at an angle and has a loop with an inner diameter. The inner diameter is configured to encircle a skin irritation. The loop is configured to apply an inward pressure to the skin irritation in response to pressing the loop against skin surrounding the skin irritation using the curved elongated handle.

20 Claims, 17 Drawing Sheets

(56) References Cited

U.S. PATENT DOCUMENTS

| | | | | |
|---|---|---|---|---|
| 5,910,147 A | * | 6/1999 | Rosenberg | A61B 17/54 606/181 |
| D436,689 S | * | 1/2001 | Ortiz | D28/9 |
| 2016/0331409 A1 | * | 11/2016 | Lampson | A61B 90/30 |

* cited by examiner

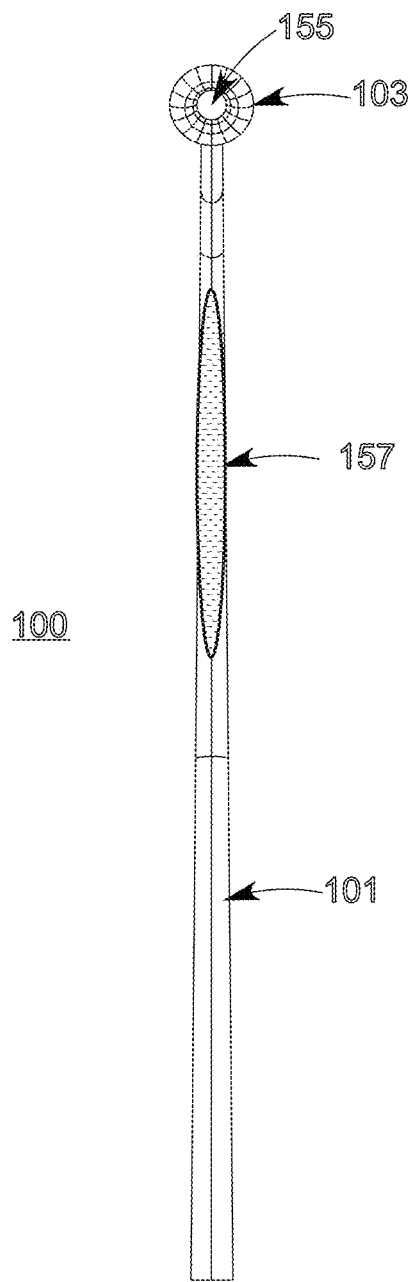
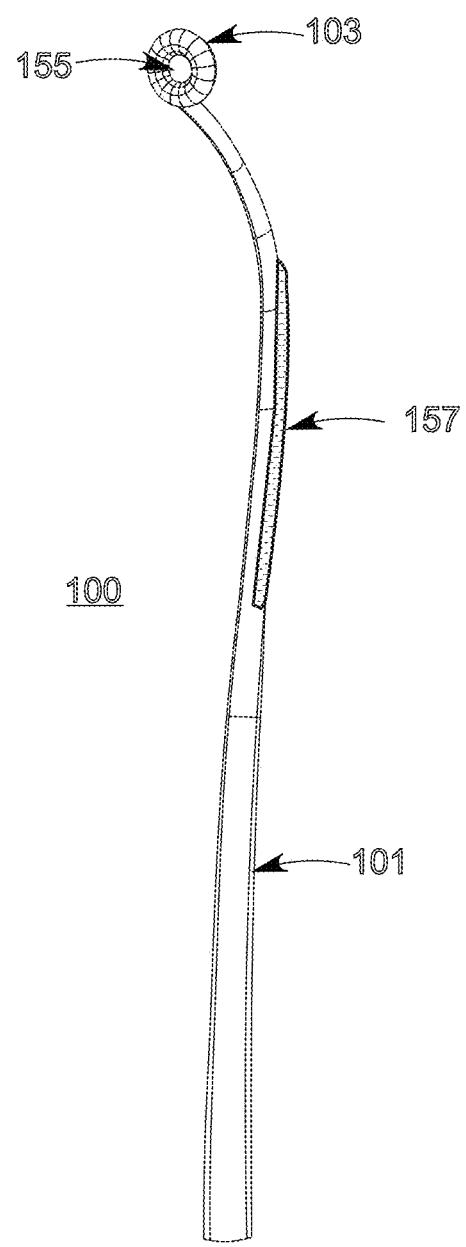
FIG. 2A
FIG. 2B

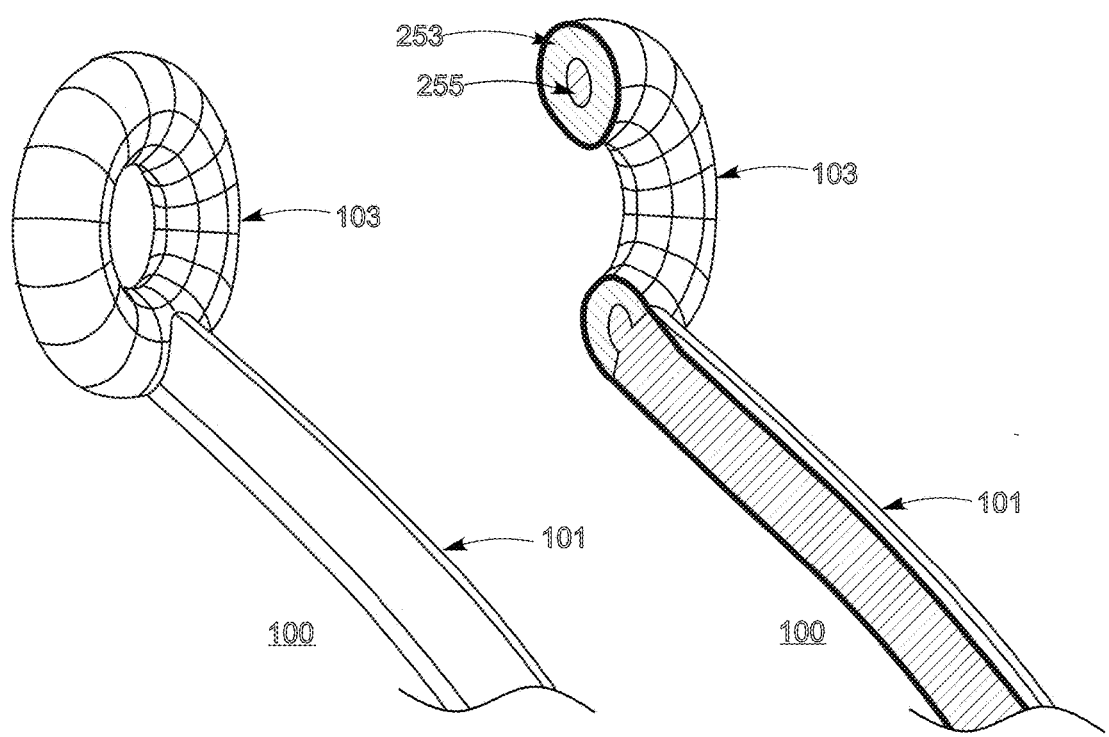
FIG. 4A
FIG. 4B
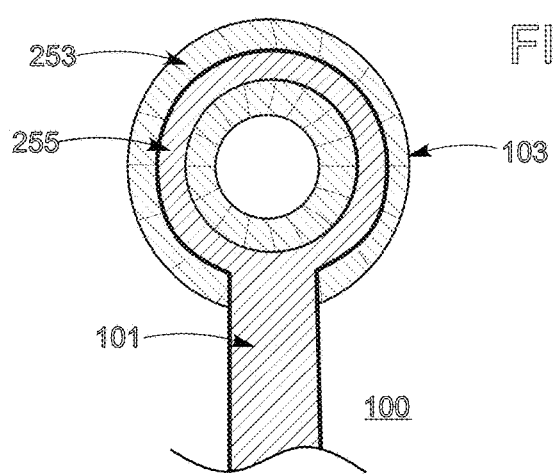
FIG. 4C

ACNE EXTRACTOR FOR TREATING SUPERFICIAL ACNE

TECHNICAL FIELD

This disclosure herein relates generally to dermatology and, more specifically, an acne extractor for treating superficial acne.

BACKGROUND OF THE INVENTION

There is a broad range of acne conditions that are caused by clogged or inflamed sebaceous glands or an increased presence of pimple-causing bacteria on your skin. Many dermatologists recommend seeking professional treatment for any acne because the wrong treatment can cause bacterial infection, swelling, and long-term scarring. The issue, however, is that patients with acne cannot access professional treatment due to geographical constraints, time constraints, or financial constraints. As a result, patients may resort to unsuitable and non-sterile alternatives at home for which patients have no proper training or knowledge.

Some at-home devices for treating acne include fully rigid metal devices that are painful and can cause irritation when pressed too firmly on the skin. More worrisome, improper extraction techniques with rigid metal devices can increase the likelihood of bad patient outcomes, including an amplified acne outbreak, or even scarring. There is a need to improve the at-home experience of treating superficial acne such as comedones, blackheads, and whiteheads.

SUMMARY OF THE INVENTION

The present disclosure provides methods, systems, and articles of manufacture for an acne extractor for treating superficial acne.

In one aspect, there is provided an acne extractor for treating superficial acne. The acne extractor includes a curved elongated handle having a distal end. A head is coupled to the distal end of the curved elongated handle. The head extends from curved elongated handle at an angle and has a loop with an inner diameter. The inner diameter is configured to encircle a skin irritation. The loop is configured to apply an inward pressure to the skin irritation in response to pressing the loop against skin surrounding the skin irritation using the curved elongated handle.

In some variations, the curved elongated handle and the head are formed from an elastomeric material and wherein the elastomeric material forming the curved elongated handle and the head are homogeneous. Further, the head is selectively coupled to the curved elongated handle. Additionally, the curved elongated handle includes a button to decrease the inner diameter to create a pinching effect at the loop.

In some variations, the head includes a pressure sensor communicatively coupled to a speaker for emitting a sound in response to the pressure sensor detecting a pressure reading exceeding a pressure threshold. Further, the head includes a first portion with a first density and a second portion with a second density. Additionally, the first portion is configured to flatten in response to being pressed against the skin thereby creating the inward pressure on the skin irritation.

In some variations, the head includes a first side and a second side, the first side including at least one of a plurality of recessions or a plurality of protrusions. Further, the curved elongated handle has a tightening knob configured to adjust the angle of the head relative to the curved elongated handle. Additionally, the head has a circular shape.

In another aspect, there is provided another acne extractor for treating superficial acne. The acne extractor includes a curved elongated handle having a distal end and a proximate end. The first head is coupled to the distal end of the curved elongated handle. The first head extends from the curved elongated handle at an angle and has a first loop with a first inner diameter. The first inner diameter configured to encircle the skin irritation. The first loop is configured to apply inward pressure to the skin irritation in response to pressing the first loop against skin surrounding the skin irritation using the curved elongated handle.

In some variations, the proximate end is hollow and is configured to store a selectively removable piercing appendage. Further, the acne extractor also includes a second head coupled to the proximate end of the curved elongated handle. The second head extends from the curved elongated handle at an angle and has a second loop with a second inner diameter. The second inner diameter configured to encircle the skin irritation. The second loop is configured to apply inward pressure to the skin irritation in response to pressing the second loop against skin surrounding the skin irritation using the curved elongated handle.

In some variations, the curved elongated handle, the first head, and the second head are formed from an elastomeric material and wherein the elastomeric material forming the curved elongated handle, the first head, and the second head are homogeneous. Further, the first head and the second head are selectively coupled to the curved elongated handle. The first head is larger than the second head and wherein the first head is more adhesive than the second head. Additionally, the first head has a different shape than the second head. Further, the first head has a different hardness than the second head. Additionally, the first head is configured to be selectively attached to the proximate end and the second head is configured to be selectively attached to the distal end.

In yet another aspect, there is provided another acne extractor for treating superficial acne. The acne extractor includes an elongated handle having a distal end. The acne extractor includes a head coupled to the distal end of the elongated handle. The head extends from the elongated handle at an angle and has a loop with a first side and a second side. The first side is configured to flatten in response to being pressed against skin surrounding the skin irritation thereby creating an inward pressure on the skin irritation. The first side of the loop is configured to press against the skin surrounding the skin irritation. The loop is configured to apply inward pressure to the skin irritation in response to pressing the loop against the skin surrounding the skin irritation using the elongated handle.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes, it should be readily understood that such features are not intended to be limiting. The claims that follow this disclosure are intended to define the scope of the protected subject matter.

BRIEF DESCRIPTION OF THE DRAWINGS

The embodiments herein may be better understood by referring to the following description in conjunction with the accompanying drawings in which like reference numerals indicate identically or functionally similar elements, of which:

FIG. 2A shows an example of a schematic of a top view of the acne extractor with a textured grip for improving ergonomics;

FIG. 2B shows an example of a schematic of a left bottom view of the acne extractor with a textured grip;

FIG. 4A shows an example of a top-left zoomed view of the acne extractor to show the details of the head;

FIG. 4B shows an example of a cross-sectional view of the acne extractor that illustrates the details of the rigid material of the handle embedded inside the elastomeric material and the rigid material of the handle extending through the head;

FIG. 4C shows an example of a cross-sectional view of the acne extractor illustrating the detail of the interior of the head in which the rigid materials are engulfed inside the elastomeric material;

DETAILED DESCRIPTION OF THE DRAWINGS

Figure 1A:
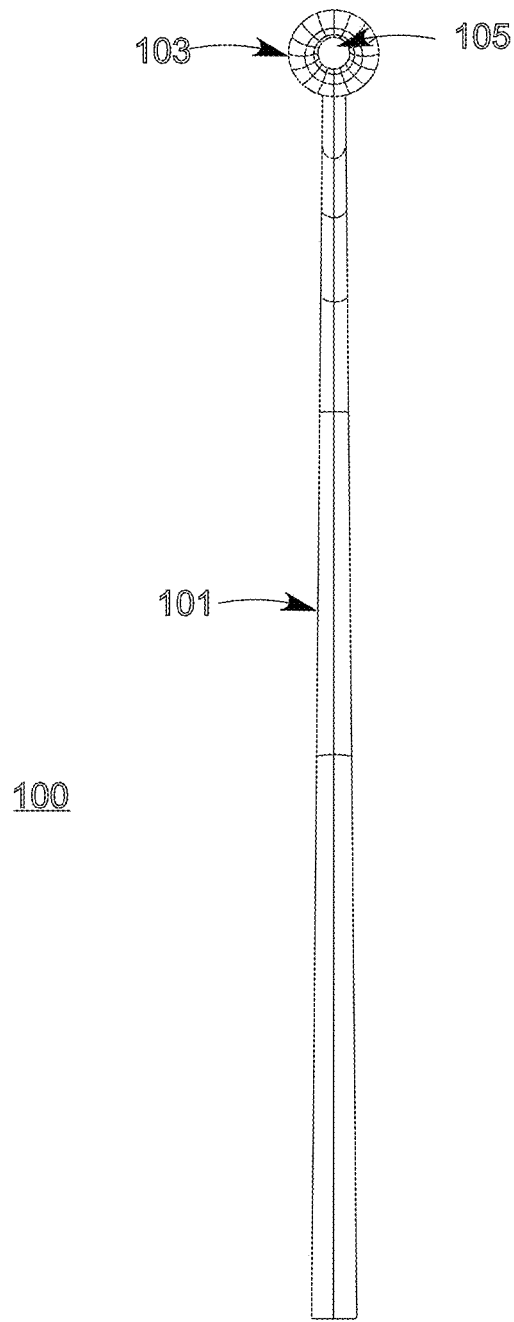
FIG. 1A shows an example of a schematic of a bottom view of the acne extractor.

Unlike other at-home alternatives that tend to be non-sterile and unsuitable for treating acne, the acne extractor described herein is less painful, inhibits swelling, and minimizes scarring while treating acne. The acne extractor also reduces post-extraction infection if using anti-bacterial silicone or similar as the material for the head of the acne extractor. The acne extractor described herein is particularly effective at treating acne conditions, including comedones, whiteheads, and blackheads.

In conjunction with the proper education, the extractor with an anti-bacterial surface may reduce the probability of post-treatment infection while being engineered to reduce the pressure needed for extraction, all while being gentler than what is currently available.

The acne extractor may operate to extract acne conditions by creating a pinching effect with the head. The pinching effect is created by applying a downwards pressure using the handle of the acne extractor. The downwards pressure may compress an elastomeric material and cause the elastomeric material to flatten. Flattening the elastomeric material may create an inward pressure to gently push the acne condition upward and outward.

The disclosure herein describes a unique acne extractor that incorporates elastomeric materials into the head to create a gentle interface between the extractor and the skin. This gentle interface improves user experience and outcomes by reducing pain, inhibiting swelling, and minimizing scarring in comparison to other acne treatment devices. The acne extractor incorporates elastomeric material into the head that produces an active pinching effect when pressure is applied to the skin through the head of the extractor. The pinching effect created by flattening the elastomeric material in the head actively reduces pain experienced while performing an extraction and reduces the likelihood of irritation and scarring in comparison to fully rigid acne extractors.

The design of the acne extractor offers several advantages of other acne extraction techniques. For example, the acne extractor described herein has a gentle interface between the acne extractor and the skin by integrating a soft material in the head of the acne extractor. This integration reduces the chance of scarring and decrease the patient's pain, thereby improving the extraction experience. In contrast, other acne extraction techniques apply rigid metal directly to the skin, increasing the likelihood of pain and scarring if misused.

In addition to reducing pain and scarring, the soft material on the acne extractor can also be shaped in a way that can create an "active pinching effect" which can create variable inwards pressure on the skin depending on how hard the acne extractor is being pressed on the skin. This can mimic fingers pressing with downwards pressure while also increasing inwards pressure, which helps to extract the acne in a way that traditional acne extractors cannot. The acne extractor according to the present disclosure can extract acne, including comedones, with less pressure applied downwards onto the skin. By applying pressure downwards and inwards, comedones and other acne conditions may be able to be extracted with less force.

Figure 1B:
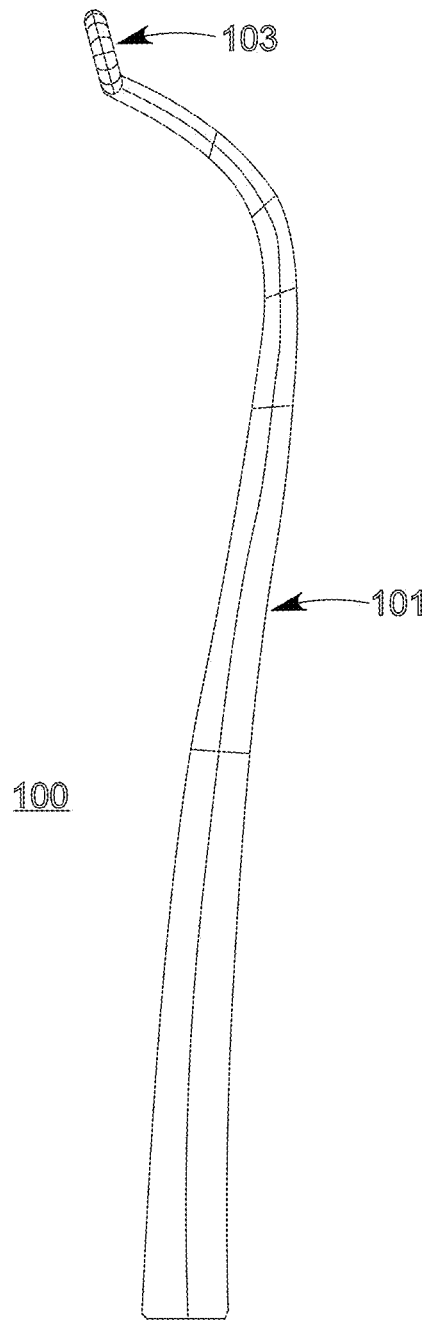
FIG. 1B shows an example of a schematic of a left side view of the acne extractor.

FIGS. 1A-1B are examples of a schematic of an acne extractor 100 for pinching and extracting skin irritations. The acne extractor may include a curved elongated handle 101. The curved elongated handle 101 may have a distal end and a proximate end. A head 103 may be coupled to the distal end of the curved elongated handle 101. The head 103 may extend from the curved elongated handle 101 at an angle and may have a loop with an inner diameter. The inner diameter may be configured to encircle a skin irritation wherein the loop is configured to apply an inward pressure to the skin irritation in response to pressing the loop against skin surrounding the skin irritation using the curved elongated handle 101. The handle 101 of an acne extractor 100 may be made from a material with rigid or semi-rigid properties. The material may be configured to support head 103 against the skin for extraction without failing/breaking. The handle 101 may have a first curve and a second curve/bend. The handle 101 may include rigid parts and/or elastomeric parts to optimize the ergonomic feel and function for acne extraction. The first curve may be proximate to the middle of the handle 101. The second curve may be proximate to where the elongated handle 101 connects to the head 103. The head 103 of the acne extractor 100 may be selectively coupled to the curved elongated handle 101.

FIG. 1A shows an example of a schematic of a bottom view of the acne extractor 100. FIG. 1B shows an example of a schematic of a left-side view of the acne extractor 100. The handle 101 may be bent at an angle so the user does not have to hold their hand at an awkward angle while performing acne extraction.

The materials of the acne extractor 100 may be manufactured separately and then assembled or manufactured as one piece. The interface between the "soft" head 103 material and handle 101 (i.e., underlying frame and handle) of the acne extractor 100 may be made by adhering the soft material, imbedding it within or around the handle 101, or making it removable so it can be cleaned or transferred to a different extractor handle 101 or discarded separately from the handle 101. In some embodiments, a one-piece acne extractor 100 can be molded where there are varying densities of a homogeneous material that create a soft material head 103 and a hard handle 101.

The material of the head 103 can be integrated with the handle 101 (e.g. a plastic or metal frame) using different manufacturing techniques. For example, the material of the head 103 can be molded directly onto the underlying frame of acne extractor 100 after the handle 101 is already attached. In other embodiments, the material of the head 103 can be molded separately and then attached (i.e., glued) onto the acne extractor 100. In other embodiments, the material of the head 103 can be constructed of multiple pieces that are made and assembled before installing onto an underlying frame of the head 103 of the acne extractor 100. In some embodiments, the head 103 of the acne extractor 100 may be made from a polymer casting. To reduce the likelihood of post-extraction infection, the material of the head 103 can have antibacterial properties such as antibacterial silicone.

Polymer casting and injection molding are both feasible manufacturing methods for the head 103. Polymer casting and injection molding may adhere the head 103 to the handle 101 of the acne extractor 100 so the interface between both is strong and durable. Further, the polymer casting and injection molding may produce a high-quality acne extractor 100 that may retain its shape and function over many extractions. The head 103 of the acne extractor 100 may experience wear due to compression at various pressures depending on extraction type. Dual-shot injection molding may allow the elastomeric material of the head 103 and rigid material of the handle 101 to adhere while heated, creating a strong permanent bond.

FIGS. 2A-2B show examples of an acne extractor 100 for pinching and extracting skin irritations. The acne extractor 100 may include a curved elongated handle 101 having a distal end and a proximate end. A head 103 may be coupled to the distal end of the curved elongated handle 101. The head 103 may extend from the curved elongated handle 101 at an angle and may have loop with an inner diameter 155. The inner diameter 155 may be configured to encircle a skin irritation, wherein the loop is configured to apply an inward pressure to the skin irritation in response to pressing the loop against skin surrounding the skin irritation using the curved elongated handle 151.

FIG. 2A shows an example of a schematic of a top view of an acne extractor 100 with a textured grip 157 for improving ergonomics. FIG. 2B shows an example of a schematic of a left bottom view of the extractor 150 with a textured grip 157. The textured grip 157 may be on the backside of the handle 101 or proximate to the first curve/bend in the elongated body of the handle 101. To optimize the form, fit, and function of the acne extractor 100, the materials for the handle 101 can be a polymer-like plastic or rubber, or a metal like stainless steel or titanium, and can be manufactured using methods like 3D printing, injection molding, casting, cutting, machining, casting, folding, welding, punching, shearing, stamping and/or the like. The acne extractor 100 may have curved elongated handle 101 and the head 103 that may be formed from elastomeric material and wherein the elastomeric material forming the curved elongated handle 101 and the head 103 are homogeneous.

In embodiments, there can be a protective barrier on the handle 151 of the acne extractor 100 to prevent the direct contact of the handle 151 on the skin of the user. This may give the user more grip or protect the extraction site from touching the handle 151. This protective barrier can be made of any material that may be soft on the skin, such as an elastomeric material like silicone.

Figure 3:
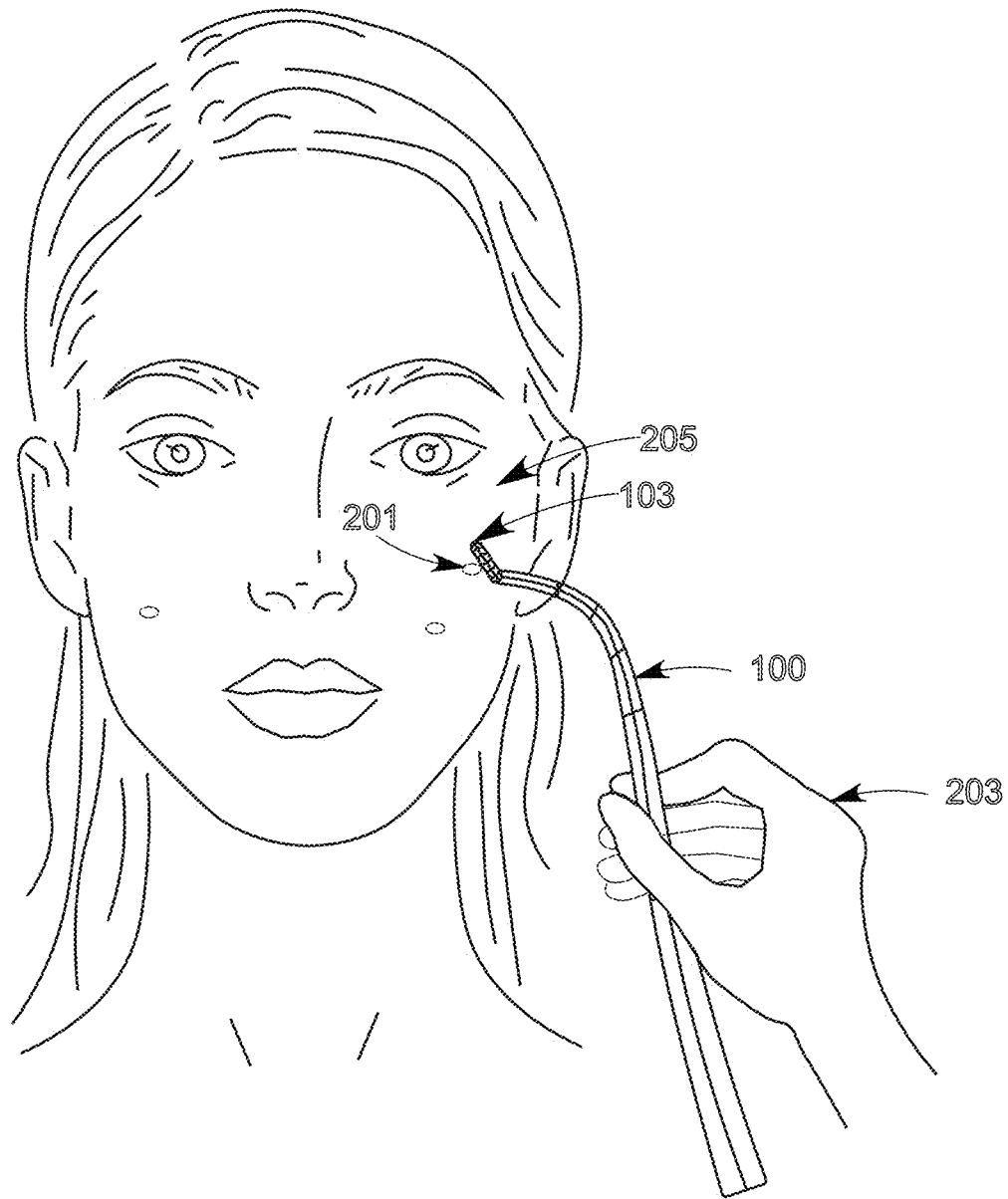
FIG. 3 shows an example of a schematic depicting an example of how the acne extractor is used by pressing the acne extractor down on the pimple with the hand.

FIG. 3 shows an example of a schematic depicting how an acne extractor 100 is used by pressing the extractor 100 down on acne 201 with a hand 203. Before using the acne extractor 100, it is recommended that the user applies a warm compress such as a damp, warm washcloth, to the affected area to help soften and open up the pore containing the acne 201. Next, the skin 203 and acne extractor 100 may be sanitized with alcohol. The acne extractor 100 may be held in the acne 201 to create a downward force through the acne extractor's 100 head 103 and onto the skin 205. The head 103 of the acne extractor 100 may have an aperture 105 (see e.g., FIG. 1A) to be aligned with the acne 201, and then the pressure downwards surrounding the acne 201 may create an effect where the acne 201 may burst out of the skin's pore (FIGS. 5A-5C), hence cleaning the skin 205 of the acne 201. The aperture 105 of the head 103 of the acne extractor 100 may have negative space, meaning that the center may not directly apply pressure to the acne 201. Instead, the outer edges of the extractor's head 103 may apply pressure around the perimeter of the acne 201, which may apply pressure inwards towards the acne 201. After the acne 201 is extracted, the user may wipe it away with a sterile object such as cotton swab, cloth, or gloved finger. The skin 205 may then be washed gently with soap and water to remove any lingering bacteria.

FIGS. 4A-4C are examples of the head 103 of an acne extractor 100 that details the interface between the elastomeric material 253 and rigid material 255 of the head 103. The material properties, size, relative position, and shape of the materials of the head 251 may significantly impact the function of the head 103 of the acne extractor 100 as it relates to acne extractions. The extractor 100 in FIGS. 4A-4C includes a curved elongated handle 101 having a distal end and a proximate end and a head 103 coupled to the distal end of the curved elongated handle 101. The head 103 extends from the handle 101 at an angle and has an inner loop made of rigid material 255 and outer loop made from elastomeric material 253. Both loops have an inner diameter configured to encircle a skin irritation, wherein the loops apply an inward pressure to the skin irritation in response to pressing the head 103 against skin surrounding the skin irritation using the curved elongated handle 101. The elastomeric material 253 may compress and flatten in response to being pressed against the skin, which creates inward pressure toward the center of the acne in addition to the downward pressure. The function of the rigid material 255 is to apply downward pressure perpendicular to the surface of the skin through the handle 101 to the elastomeric material 253. The elastomeric material 253 may transfer part of that pressure linearly down to the perimeter of the acne but also displaces pressure outwards away from the center of head loop as it becomes compressed and flattened against the skin, which creates an additional inward pinching pressure on the acne. The head 103 may be selectively coupled to the handle 101 and may have a first side having a first opening and a second side having a second opening. The first opening having a greater diameter than the second opening. The first side may be configured to press against the skin surrounding the skin irritation. These different diameters may help improve the pinching effect of the head 103 when compressed on the skin by adding inward forces to the forces already generated by the flattening of the elastomeric material 253. FIG. 4A shows an example of a top-left zoomed view of an acne extractor 100 to show the details of the head 103. FIG. 4B shows an example of a cross-sectional view of the acne extractor 100 that illustrates the details of the rigid material 255 of the handle 101 embedded inside the elastomeric material 253 and the rigid material 255 of the handle 101 extending through the head 103. FIG. 4C shows an example of a cross-sectional view of the acne extractor 100 illustrating the detail of the interior of the head 103 in which the rigid material 255 in the head 103 is engulfed inside the elastomeric material 253.

Materials for the elastomeric part of the head 103 as shown in FIGS. 4A, 4B, and 4C can be (but not limited to) polyurethane, epoxy, polyether, polyesters, acrylic, or silicone. The material properties of the head 103 can be altered as the physical design changes to accommodate mechanical properties of the overall function of the extractor in relation to extracting acne. In addition, the material of the head 103 can have anti-bacterial sterile properties to reduce the likelihood of infection and the frequency of cleaning/sterilization that is necessary.

Figure 5A:
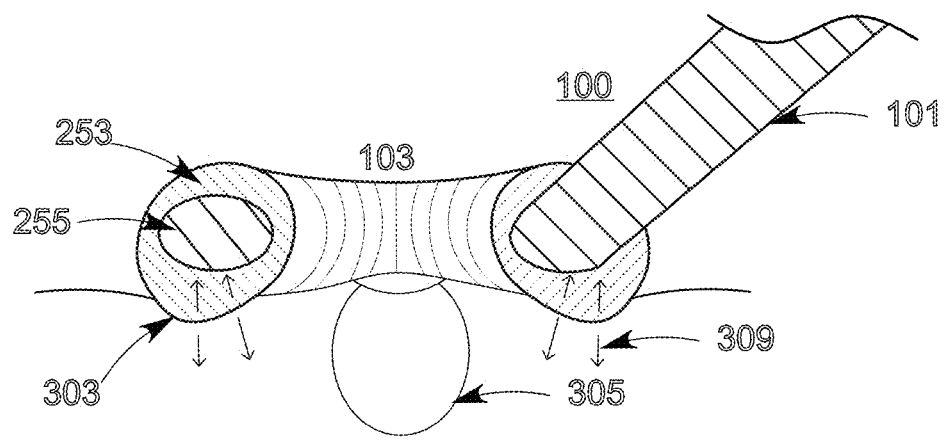
FIG. 5A shows an example of a cross-sectional view of the head of the acne extractor gently pressed against the skin with a downwards force toward skin.
Figure 5B:
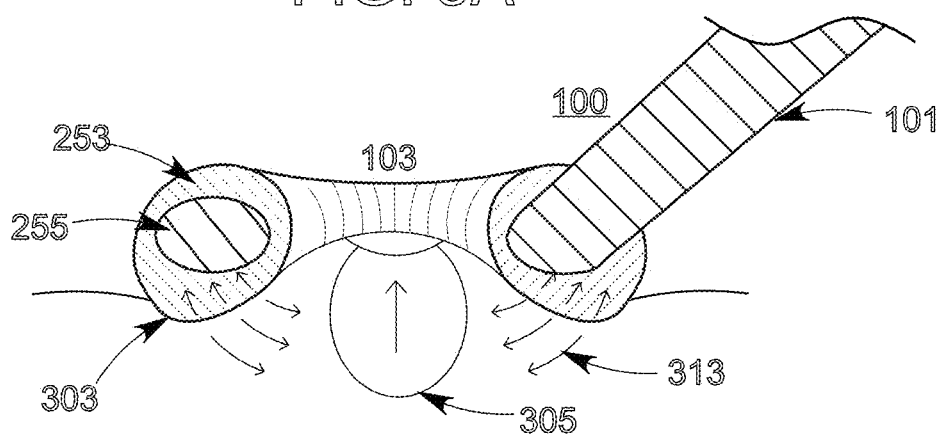
FIG. 5B shows an example of a cross-sectional view of the head of the acne extractor being pressed against the skin with a greater downwards force toward the skin for increasing the internal pressure of the acne.
Figure 5C:
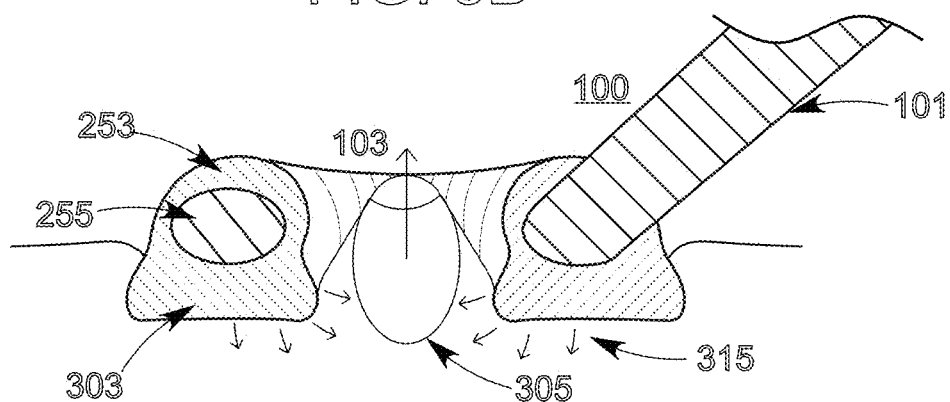
FIG. 5C shows an example of a cross-sectional view of the head of the extractor being pressed against the skin with a downwards force toward the skin sufficient for increasing the extracting the acne.

FIGS. 5A-5C are cross-sectional views of the head 103 of the acne extractor 100 being pressed onto the skin 303 to extract acne 305 to illustrate the pinching effect of the elastomeric material 253. FIG. 5A shows an example of a cross-sectional view of the head 103 of the extractor 100 at the beginning stages of acne 305 extraction, where the head 103 gently pressed against the skin 303 with a downwards force 309 toward the skin 303. The rigid material 255 embedded within the elastomeric material 253 may provide structural support to the head 103 and may allow for force transfer (309, 313, 315) between the user to the handle 101 to the skin 303 around perimeter of the acne 305. FIG. 5B shows an example of a cross-sectional view of the head 103 of the extractor 100 being pressed against the skin 303 with a greater downwards force 313 toward the skin for increasing the internal pressure of the acne 305. Since more force 313 is being applied to the skin 303 by the head 103, the elastomeric material 253 is beginning to deform and flatten against the skin 303 and the displaced material is beginning to create a pinching effect on the acne 305 because the applied force 313 is now down and inward toward the acne 305. FIG. 5C shows an example of a cross-sectional view of the head 103 of the extractor 100 being pressed against the skin 303 with a downwards force 315 toward the skin 303 that is displacing and flattening more elastomeric material 253 and creating a more significant pinching effect, sufficient for extracting the acne 305. Because the force from the user is being displaced from the vertical axis and partially translated inward toward the acne 305, it may require less force to produce the same extraction in comparison to a fully rigid head 103 with no elastomeric properties. This is just one example of a head 103 of an acne extractor 100, and any acne extractor 100 with a soft elastomeric material 253 on the head 103 may cause less bruising with the same force used, and less pain because the overall force needed may be less. This invention may produce a gentler acne 305 extraction because of the head's 103 elastomeric properties.

Figure 6A:
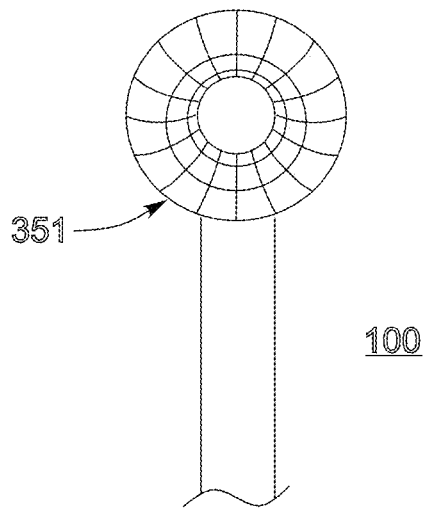
FIG. 6A shows an example of a schematic of a circular doughnut-shaped head of the extractor.
Figure 6B:
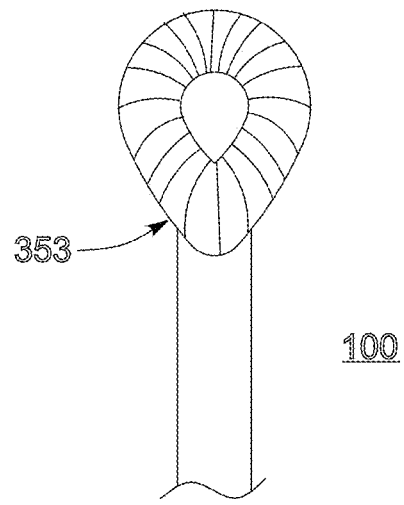
FIG. 6B shows an example of a schematic of a teardrop-shaped head of the acne extractor.
Figure 6C:
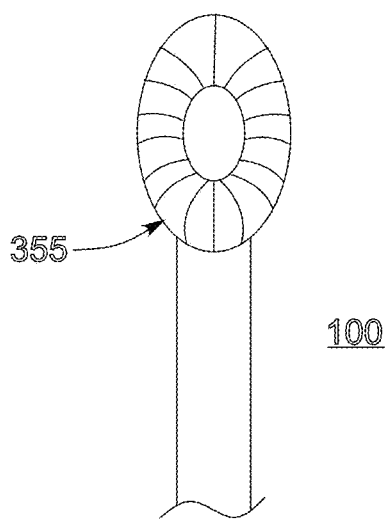
FIG. 6C shows an example of a schematic of an oval-shaped head of the acne extractor.
Figure 6D:
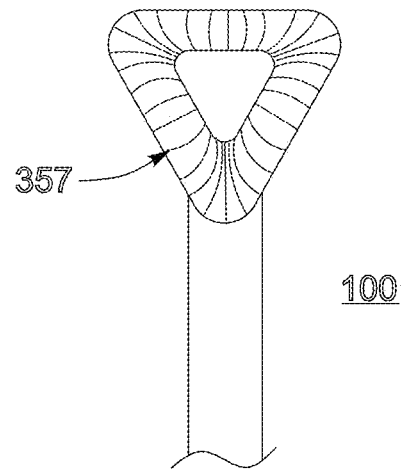
FIG. 6D shows an example of a schematic of a triangular-shaped head of the acne extractor.

FIGS. 6A-6D are examples of various shapes of the head 103 of acne extractors 100. Different shapes of heads 103 may be used for different types of extractions to optimally extract the acne with as little damage to the skin as possible to improve the rate of recovery and overall outcome post extraction. FIG. 6A shows an example of a schematic of a circular doughnut-shaped head 351 of the acne extractor 100. This shape can be useful for acne that needs uniform pressure applied around its circumference to gently expel its contents. FIG. 6B shows an example of a schematic of a teardrop-shaped head 353 of the acne extractor 100. This head 353 shape can benefit the user by allowing them to apply a disproportionate amount of pressure through the terminal end of head 353 to one side of the acne rather than uniformly surrounding it. FIG. 6C shows an example of a schematic of an oval-shaped head 355 of the acne extractor 100. This head 355 shape can benefit a user if they want uneven pressure distribution around the circumference of their acne. FIG. 6D shows an example of a schematic of a triangular-shaped head 357 of the extractor 100. This head 357 may be beneficial for a user who has porous skin and wants to expel oil gently and efficiently, so they may use the terminal end of the head 357 to compress on their skin and pull across the surface of the skin so the acne extractor 100 acts more like a squeegee to expel excess oil than a single-focused acne. The elastomeric properties of the head 357, in combination with low-friction properties of the surface of the head 357, may reduce the likelihood of skin damage when using this technique in comparison to a fully rigid head 357. These are just a few examples of shapes and functions that the acne extractor 100 may incorporate, and not all functions of each example shape are detailed.

Figure 7A:
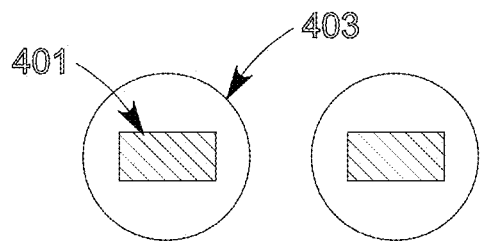
FIG. 7A shows an example of a cross-section of the head of the acne extractor having a circular profile with a rectangular rigid material embedded inside the elastomeric material.
Figure 7B:
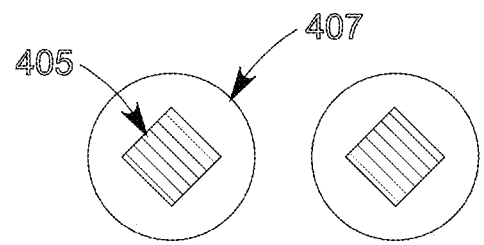
FIG. 7B shows an example of a cross-section of the head of the acne extractor having a circular profile with a rhombus rigid material embedded inside the elastomeric material.
Figure 7C:
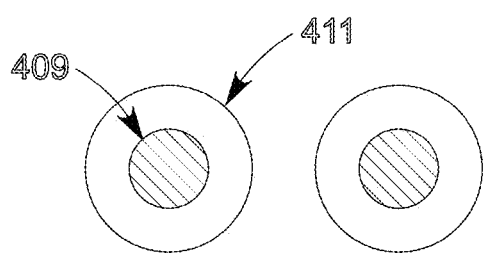
FIG. 7C shows an example of a cross-section of the head of the acne extractor having a circular profile, with a circular rigid material embedded inside the elastomeric material.
Figure 7D:
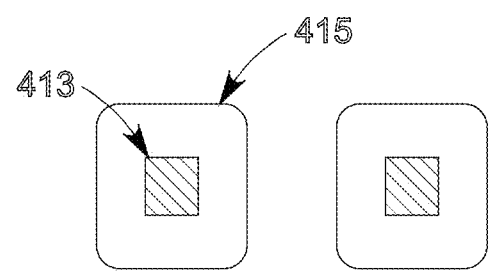
FIG. 7D shows an example of a cross-section of the head of the acne extractor having a square profile with the square rigid material embedded inside the elastomeric material.
Figure 7E:
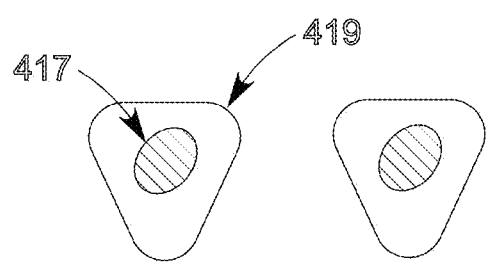
FIG. 7E shows an example of a cross-section of the head of the acne extractor having a triangular profile with the oval rigid material embedded inside the elastomeric material.

FIGS. 7A-7E are examples of different cross-sectional profiles of the head 103 of an acne extractor 100 that may make different pressure distributions on the skin. The rigid frame material 255 and elastomeric material 253 may each have different shapes that may create different pressure distributions optimized for different types of acne. FIG. 7A shows an example of a cross-section of the head 103 of the acne extractor 100 having a circular profile with a rectangular rigid material 401 embedded inside the elastomeric material 403. FIG. 7B shows an example of a cross-section of the head 103 of the acne extractor 100 having a circular profile with a rhombus rigid material 405 embedded inside the elastomeric material 407. FIG. 7C shows an example of a cross-section of the head 103 of the acne extractor 100 having a circular profile, with a circular rigid material 409 embedded inside the elastomeric material 411. FIG. 7D shows an example of a cross-section of the head 103 of the acne extractor 100 having a square profile with the square rigid material 413 embedded inside the elastomeric material 415. FIG. 7E shows an example of a cross-section of the head 103 of the acne extractor 100 having a triangular profile with the oval rigid material 417 embedded inside the elastomeric material 419. Each one of these cross-sections may produce a different result when force is applied through the acne extractor 100 to the skin, and each may have advantages for different types of extractions. As force is applied down, different force distributions may result from different shapes, even if the head 103 profile shape, as shown in FIGS. 6A-6D, stays consistent. The shape of the head 103 and the internal profile shape of elastomeric material and rigid materials all play an independently important role in affecting the function of the acne extractor 100.

Figures 8A, 8B, 8C:
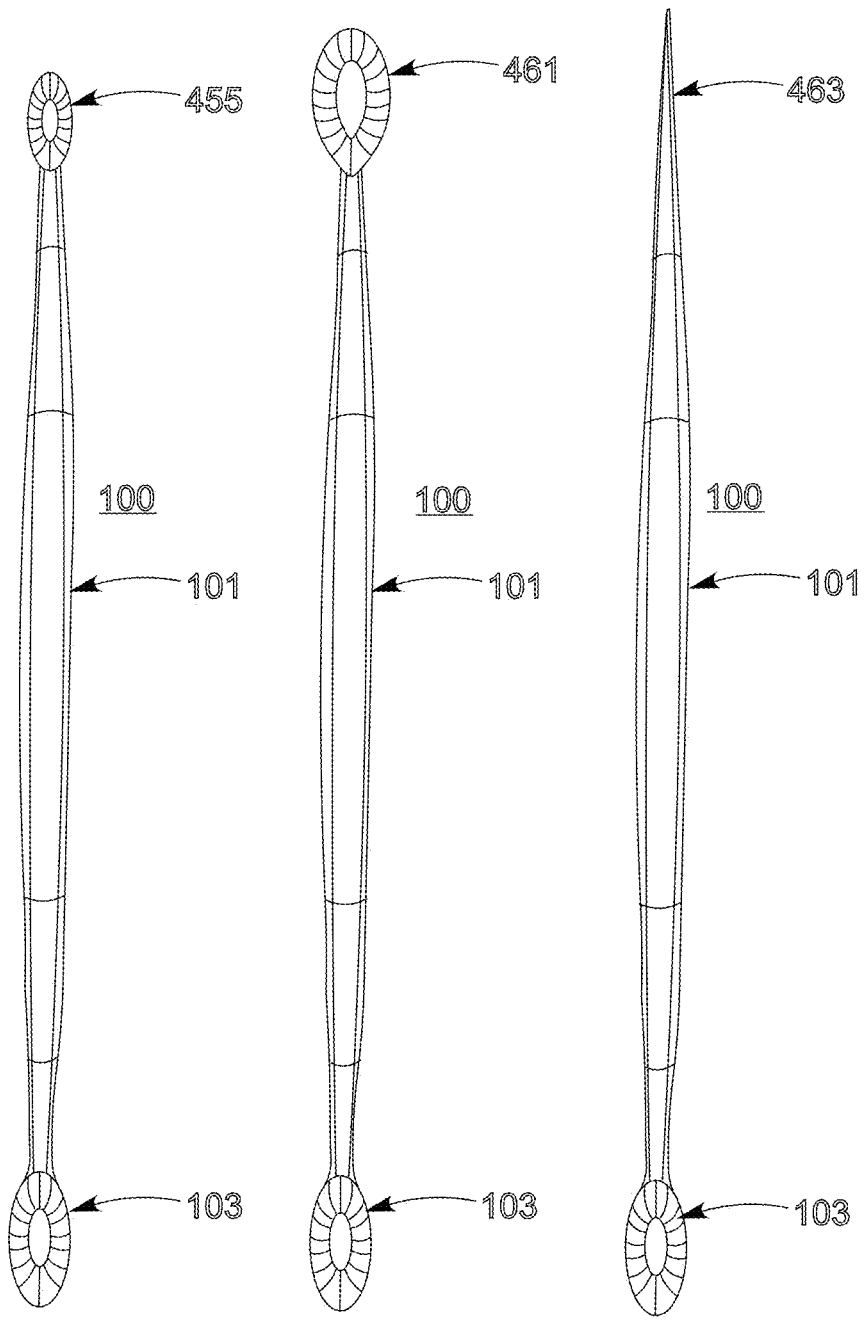
FIG. 8A shows an example of an acne extractor with a first head at a first end and a second head at a second end, where the first head is smaller than the second head.
FIG. 8B shows an example of an acne extractor with a first head at a first end and a second head at a second end, where the first head is a different shape than the second head.
FIG. 8C shows an example of an acne extractor with one sharp needle-like end for opening the pore and the other side to press and extract the acne.

FIGS. 8A-8C are examples of how the acne extractor 100 may have two different heads on opposing ends of the extractor handle 101 so the user may have more types of extractors at their disposal. FIGS. 8A-8C are examples of acne extractors 100 for pinching skin irritations, the acne extractor 100 may include a curved elongated handle 101 having a distal end and a proximate end and a first head 103 coupled to the distal end of the curved elongated handle 101, the first head 103 extending from the curved elongated handle 101 at an angle and having a first loop with a first inner diameter, the first inner diameter configured to encircle a skin irritation, wherein the first loop is configured to apply an inward pressure to the skin irritation in response to pressing the first loop against skin surrounding the skin irritation using the curved elongated handle 101.

FIG. 8A shows an example of a depiction of the acne extractor 100 with a first head 103 at a first end and a second head 455 at a second end, where the first head 103 is larger than the second head 455. FIG. 8A shows an example of an acne extractor 100 may include a first head 103 on the distal end of the handle 101 and a second head 455 that is smaller than the first head 103 coupled to the proximate end of the handle 101, the second head 455 extending from the handle 101 at an angle and having a second loop with a second inner diameter, the second inner diameter configured to encircle a skin irritation, wherein the second loop is configured to apply an inward pressure to the skin irritation in response to pressing the second loop against skin surrounding the skin irritation using the handle 101.

FIG. 8B shows an example of a depiction of the acne extractor 100 with a first head 103 at the first end and a second head 461 at a second end, where the first head 103 is a different shape than the second head 461. FIG. 8B shows an example of an acne extractor 100 may include a first head 103 on the distal end of the handle 101 and a second head 461 with a different shape than the first head 103 coupled to the proximate end of the curved elongated handle 101, the second head 461 extending from the curved elongated handle 101 at an angle and having a second loop with a second inner diameter, the second inner diameter configured to encircle a skin irritation, wherein the second loop is configured to apply an inward pressure to the skin irritation in response to pressing the second loop against skin surrounding the skin irritation using the handle 101.

Combining more than one function into one acne extractor 100 may help reduce waste and improve the experience for the user because of the accessibility of more than one function. The acne extractor's 100 curved elongated handle 101, the first head 103, and the second head 461 may be formed from elastomeric material and wherein the elastomeric material forming the curved elongated handle 101, where the material of the first head 103, and the second head 461 are homogeneous. The acne extractor 100 may have the first head 103 and the second head 461 selectively coupled to the curved elongated handle 101. The acne extractor 100 may have a first head 103 that is smaller than the second head 461 and wherein the second head 461 is more adhesive than the first head 103 to provide more grip against the skin. The first head 103 of the acne extractor 100 may have a different hardness than the second head 461. The extractor 100 may have a first head 103 configured to be selectively attached to the proximate end and the second head 461 configured to be selectively attached to the distal end.

FIG. 8C shows an example of a depiction of the acne extractor 100 with one sharp needle-like tool 463 for opening the pore and the other head 103 to press and extract the acne. FIG. 8C shows an example of an acne extractor 100 may include a first head 103 on the distal end of the handle 101 and a sharp needle-like pore opening tool 463 coupled to the proximate end of the curved elongated handle 101, the pore opening tool 463 extending from the curved elongated handle 101, wherein the pore opening tool 463 applies opens the pore of the skin irritation in response to pressing the pore opening tool 463 against the pore in the center of the skin irritation using the handle 101.

Figures 9A, 9B:
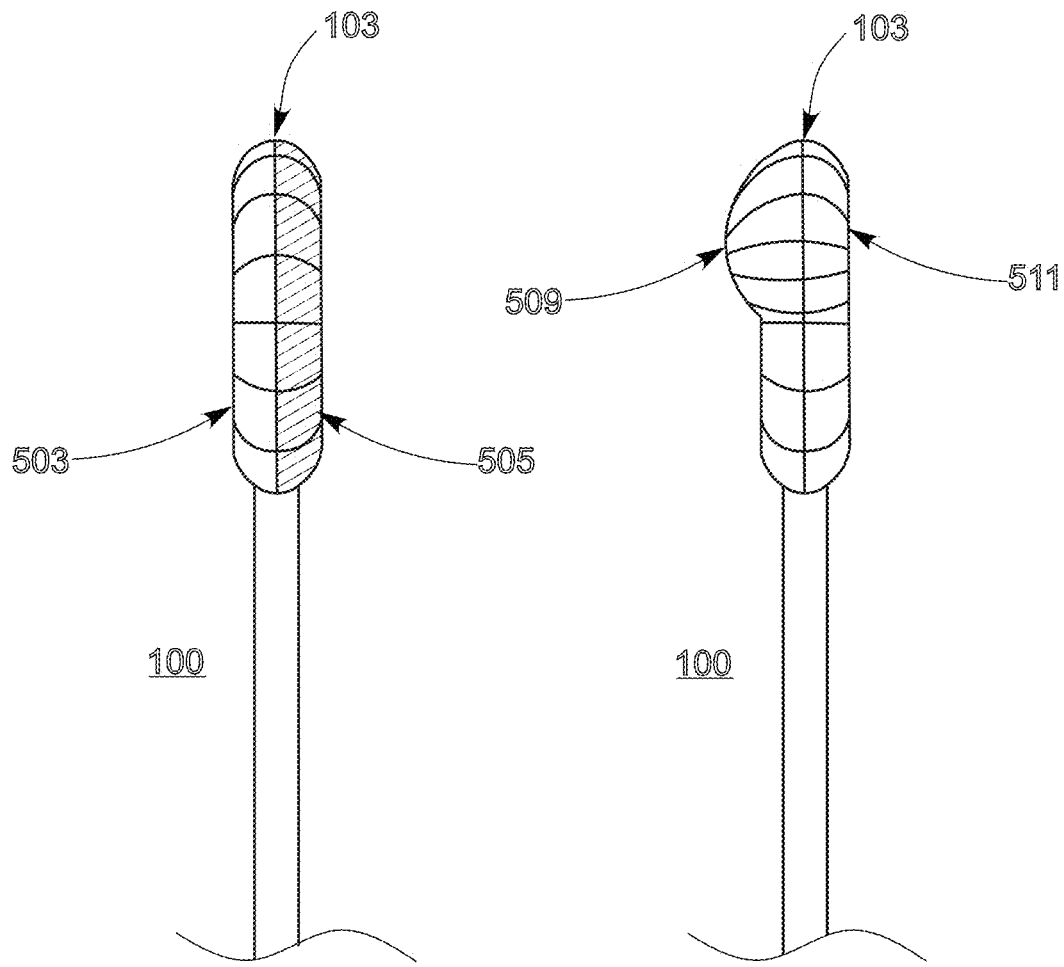
FIG. 9A shows an example of a schematic depicting the head of the acne extractor having a first density and a second density of elastomeric material.
FIG. 9B shows an example of a schematic depicting the head of the acne extractor with a first side and a second side, the first side having a protrusion and the second side having no protrusion.

FIG. 9A shows an example of a schematic depicting the head 103 of the acne extractor 100 having a first portion 503 with a first density and a second portion 505 with a second density. This may improve the user experience because it may allow them to flip between two differently optimized durometers for different types of acne extractions. For example, one shape of the single head 103 provides a certain functionality, while each side of that single head 103 may provide different levels of deformity when pressed on the acne, meaning they are optimized for different extractions such as blackhead or whitehead extractions. There can be more than two elastomeric materials in one head 103 to create unique pressure distributions that rely on material properties in addition to the shape and profile. This may be manufactured in a way that segregates or mixes elastomeric materials to produce different effects.

FIG. 9B shows an example of a schematic depicting the head 103 of the acne extractor 100 with a first side 509 and a second side 511, the first side 509 having a protrusion and the second side 511 having no protrusion. The acne extractor 100 may have a head 103 that includes a first side 509 and a second side 511, the first side 509 including at least one of a plurality of recessions or a plurality of protrusions. The acne extractor's 100 head 103 can have two shapes on opposing sides of the same head 103 to add additional functionality because they may produce different pressure distributions when pressure is applied by the extractor to the acne.

Figure 10A:
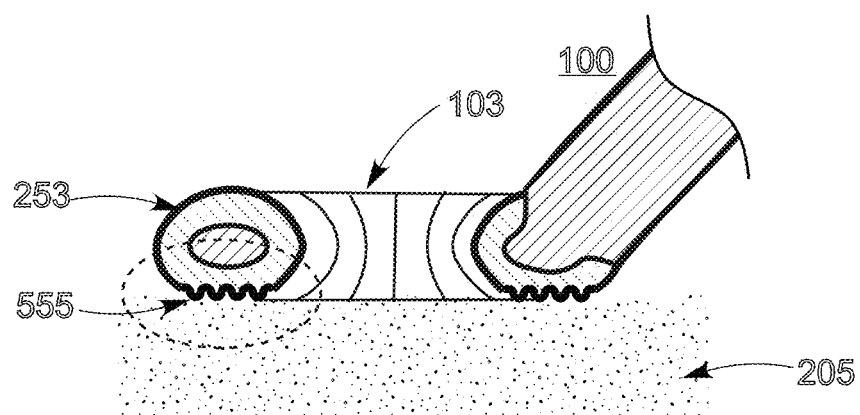
FIG. 10A shows an example of a cross-sectional view of the acne extractor, where the elastomeric material of the head is textured for improving the grip while being pressed on the skin.
Figure 10B:
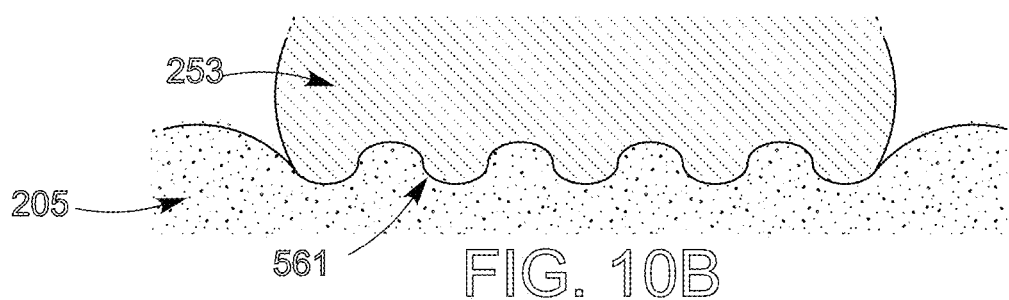
FIG. 10B shows an example of an elastomeric material of the head having a plurality of recessions for improving the grip when pressed on the skin.
Figure 10C:
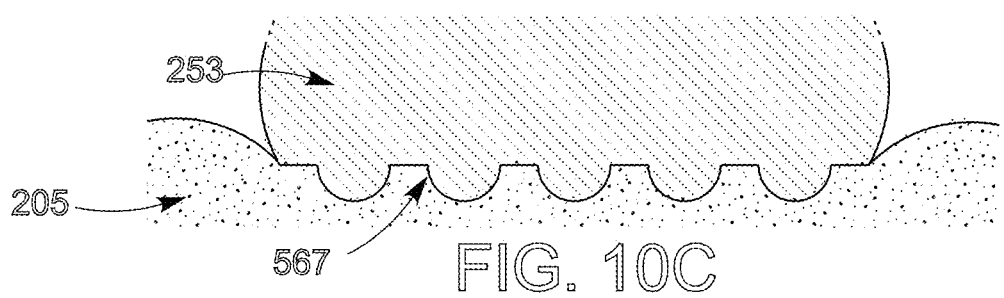
FIG. 10C shows an example of an elastomeric material of the head having a plurality of protrusions for improving the grip when pressed on the skin.
Figure 10D:
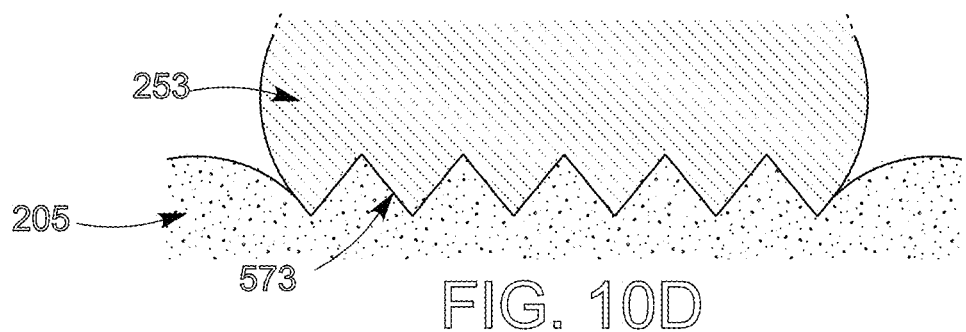
FIG. 10D shows an example of an elastomeric material of the head having a jagged pattern that improves the grip when pressed on the skin.

FIGS. 10A-10D shows examples of the acne extractor 100 with high-friction properties of the head 103 that may enable the user to have greater control of the extraction, especially if the extraction site is slippery. This added friction may be a material property such as sticky silicone or from being textured in a way that grabs the skin. FIG. 10A shows an example of a cross-sectional view of the acne extractor 100, where the elastomeric material 253 of the head 103 is textured for improving the grip 555 while being pressed on the skin 205. FIG. 10B shows an example of an elastomeric material 253 of the head 103 having a plurality of recessions for improving the grip 561 when pressed on the skin 205. FIG. 10C shows an example of an elastomeric material 253 of the head 103 having a plurality of protrusions for improving the grip 567 when pressed on the skin 205. FIG. 10D shows an example of an elastomeric material 253 of the head 103 having a jagged pattern that improves the grip 573 when pressed on the skin 205. Different textures of the head 103 may be optimized to increase friction in various environments, for different skin types, and acne conditions. The texture of the head 103 may play a role in creating a pinching effect when pressure is applied and may work in conjunction with the elastomeric properties of the head 103 to create this effect.

Figures 11A, 11B:
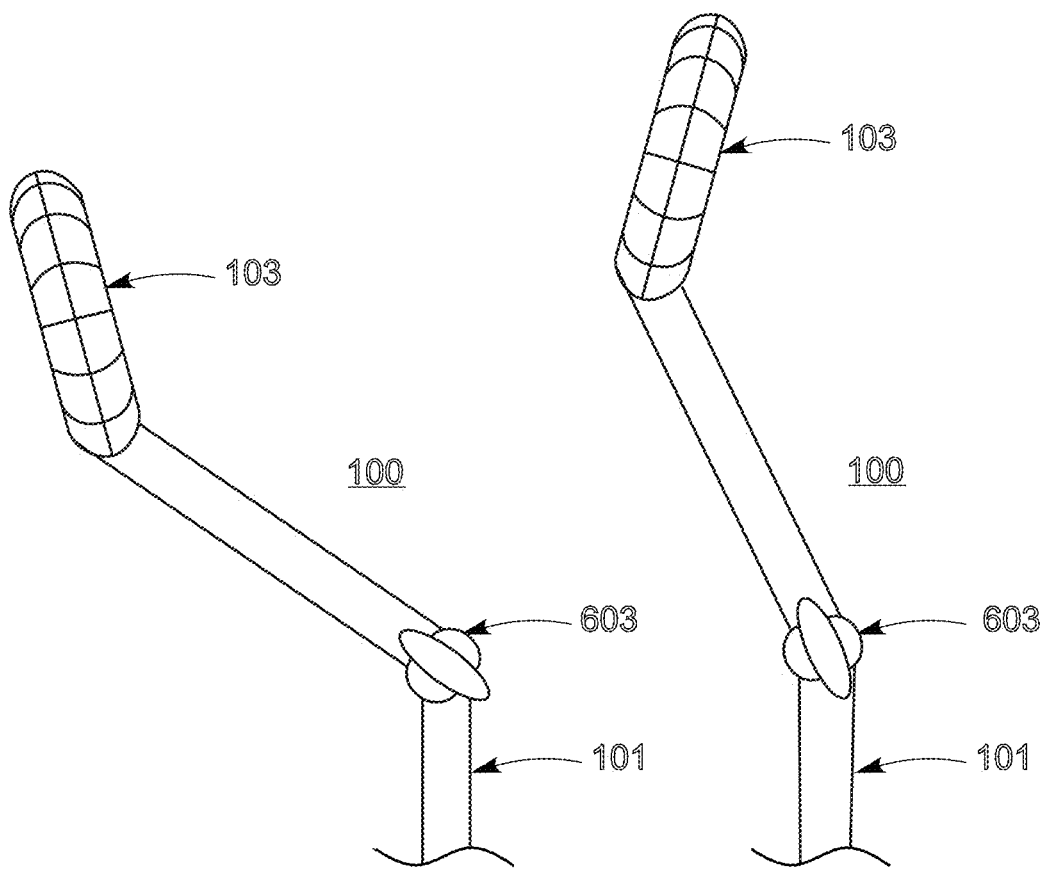
FIG. 11A shows an example of a tightening knob located at the handle of the acne extractor for adjusting the angle of the head to optimize to acne extraction on various locations on the handle.
FIG. 11B shows another example of a tightening knob located at the handle of the acne extractor for adjusting the angle of the head to optimize to acne extraction on various locations on the handle.

FIGS. 11A and 11B are examples of an acne extractor 100 wherein the curved elongated handle 101 has a tightening knob 603 configured to adjust the angle of the head 103 relative to the handle 101 to better position the acne extractor 100 for an optimal angle of extraction. FIG. 11A shows an example of a tightening knob 603 located at the handle 101 of the acne extractor 100 for adjusting the angle of the head 103 to optimize acne extraction on various locations on the body. FIG. 11B shows another example of a tightening knob 603 located at the handle 101 of the acne extractor 100 for adjusting the angle of the head 103 to optimize acne extraction on various locations on the body. To use the tightening knob 603, the user may loosen it by turning counterclockwise, which may loosen the pressure applied by the knob 603 and allow the two portions of the handle 101 to pivot around the point of the knob 603. The user may pivot the head 103 of the acne extractor 100 to create the angle that they want to use to perform their acne extraction, and then tighten the knob 603 clockwise to cinch down and put pressure on the pivot point. There may be internal properties of the pivot such as a rubber washer, or texture that may help lock the two portions of the handle 101 in place when the knob 603 is tightened.

Figures 12A, 12B:
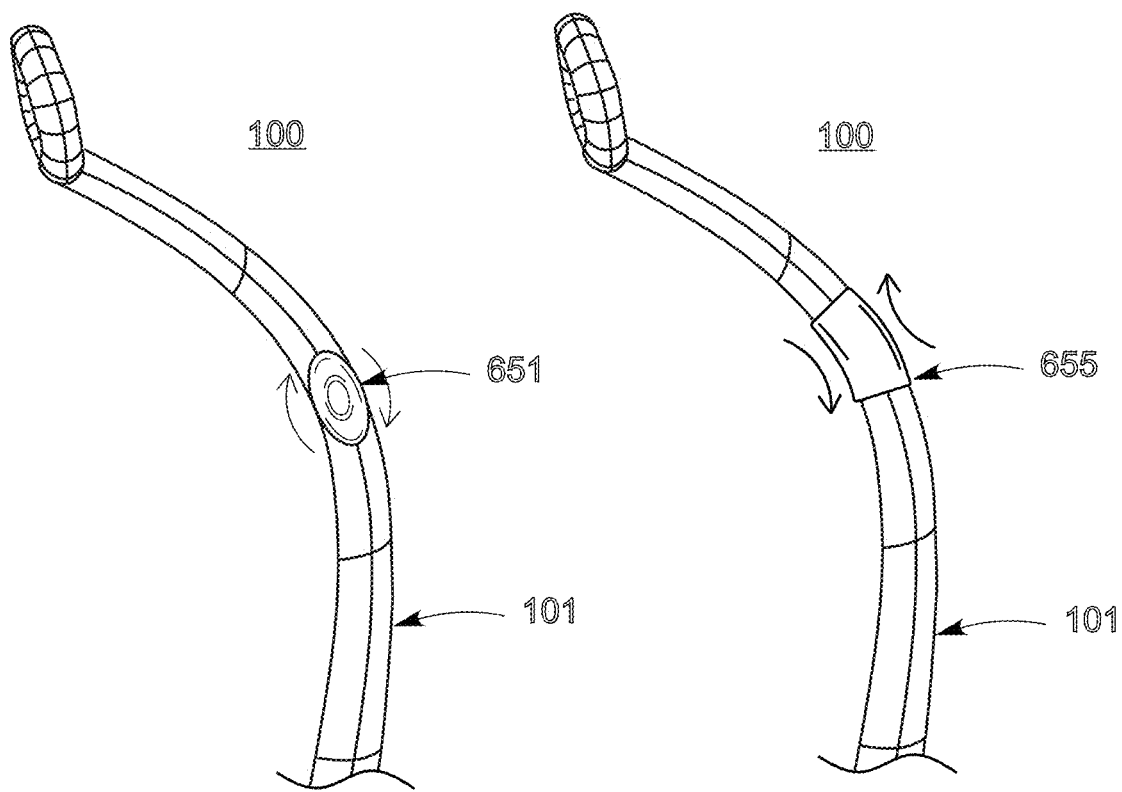
FIG. 12A shows an example of a mechanical torque device in the handle of the acne extractor for bending the acne extractor in response to applying a force.
FIG. 12B shows an example of an elastomeric material in the handle of the acne extractor for bending the extractor in response to applying a force.

FIGS. 12A and 12B show examples of how the curved elongated handle 101 of the acne extractor 100 may be composed of rigid parts and/or elastomeric parts which allows the handle 101 to partially flex during use. FIG. 12A shows an example of a mechanical torque device 651 in the handle 101 of the acne extractor 100 for bending the handle 101 in response to applying a force. Pressing too forcefully to extract acne is one of the greatest risks of extracting acne and may cause bruising that increase the likelihood of dark spots or even scarring. This may help the user by bending the handle 101 at a defined pressure to protect the user against applying too much pressure to their acne and causing damage or potential scarring. FIG. 12B shows an example of an elastomeric material 655 in the handle 101 of the acne extractor 100 for bending the acne extractor 100 in response to applying a force. This may improve the feel of the acne extraction by greeting a gentler feel when pressing down on the acne because the power transfer from the user's hand to the acne extractor 100 may be absorbed and redistributed by the deformation of the extractor's handle 101.

Figure 13A:
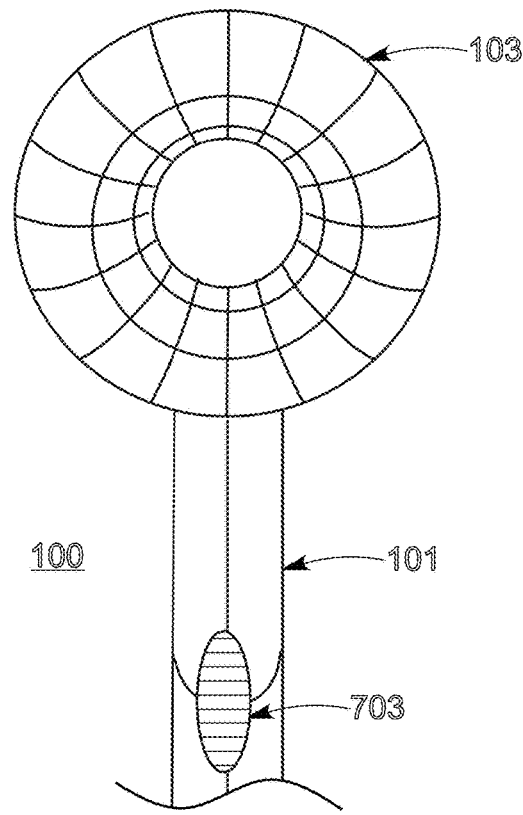
FIG. 13A shows an example of an acne extractor having a button that can cinch the area inside the head to aid in the extraction of acne.
Figure 13B:
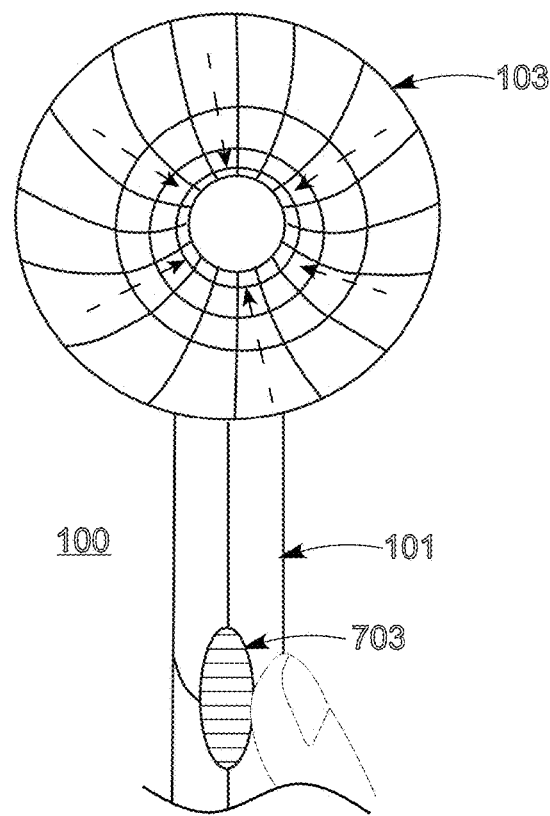
FIG. 13B shows an example of an acne extractor having a button that is being compressed by the user, and the head is cinching inward to create more pressure on the acne to aid in its extraction.

FIGS. 13A and 13B show an example of an acne extractor 100 wherein the curved elongated handle 101 includes a button 703 to decrease the inner diameter to create a pinching effect at the head's 103 loop. To use this device, a user will press the acne extractor 100 down on the skin with the center of the acne inside the loop of the head 103, and once the acne extractor 100 is stable, the user will press the button 703 to engage the cinching effect, which will help extract the acne by applying additional inward pressure. The benefit of this function may be that the acne extractor 100 may adapt its shape to extract a range of sizes of acne, in addition to other advantages not mentioned. FIG. 13A shows an example of an acne extractor 100 having a button 703 that can cinch the area inside the loop of the head 103 to aid in the extraction of acne. FIG. 13B shows an example of an acne extractor 100 having a button 703 that is being compressed by the user, and the loop of the head 103 is cinching inward to create more pressure on the acne to aid in its extraction. The function of the button 703 may also be achieved using other methods of actuation. The cinching mechanism inside the head's 103 loop may be cinched using an internal cable, not shown in the figures. Pressing the button 703 down may pull the cable into the handle 101 of the acne extractor 100, cinching the cable around the loop of the head 103.

Figure 14A:
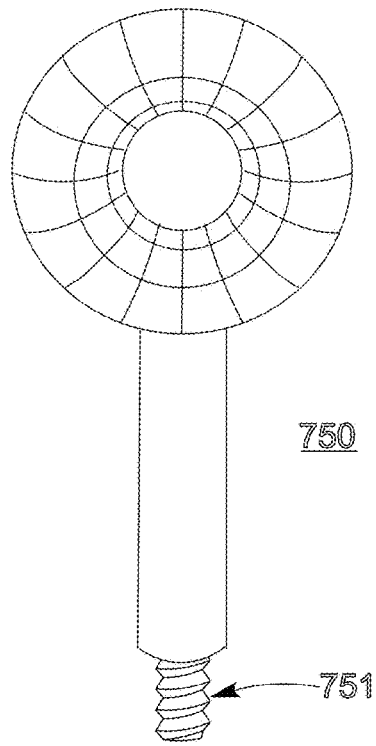
FIG. 14A shows an example of a removable head of the acne extractor having threads configured to enable the removable head to be screwed into the handle of the acne extractor.
Figure 14B:
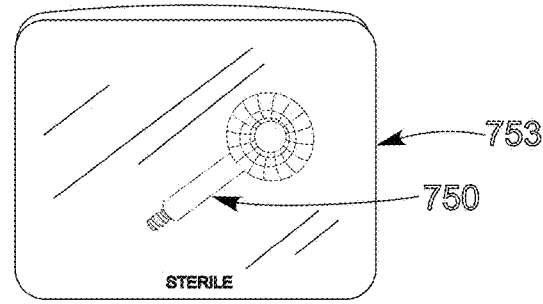
FIG. 14B shows an example of a removable head of the acne extractor sealed in a sterile bag.
Figure 14C:
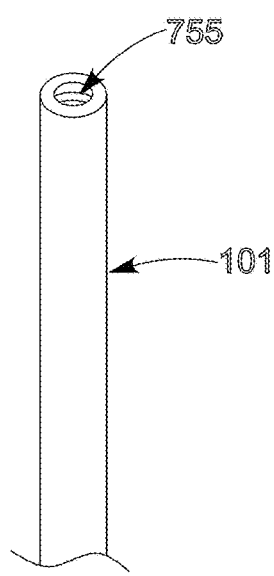
FIG. 14C shows an example of a handle of the acne extractor that having a threaded hole configured to interface with the threads of the removable head.
Figure 14D:
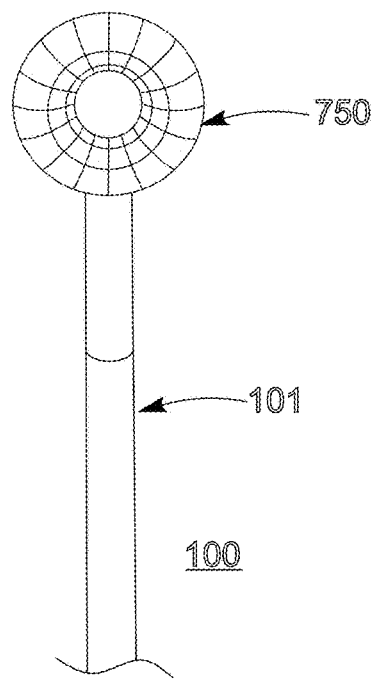
FIG. 14D shows an example of a removable head attached to the handle to create one functional acne extractor.

FIGS. 14A-14D are examples of a removable head 750 that may be purchased separately from the handle 101 of the acne extractor 100 and be contained in a sterile bag 753 until its use. FIG. 14A shows an example of a removable head 750 of the acne extractor 100 having threads 751 configured to enable the removable head 750 to be screwed into the handle 101 of the acne extractor 100. FIG. 14B shows an example of a removable head 750 of the acne extractor 100 sealed in a sterile bag 753. FIG. 14C shows an example of a handle 101 of the acne extractor 100 that has a threaded hole 755 configured to interface with the threads of the removable head 751. FIG. 14D shows an example of a removable head 750 attached to the handle 101 to create one functional acne extractor 100. The removable head 750 of the acne extractor 100 may be removed, discarded, and replaced to ensure a sterile field after each use. In this instance, the handle 101 may be reused and may attach to the removable head 750 of the acne extractor 100 using an interface such as clamping or screwing. The removable head 750 of the acne extractor 100 may be made of a less expensive material such as plastic to make this a cost-effective solution for the user, while the handle 101 may be a more durable material like stainless steel. There may be a variety of removable heads 750 for the acne extractor 100 that the user may pick depending on the type of acne they need to extract.

Figure 15A:
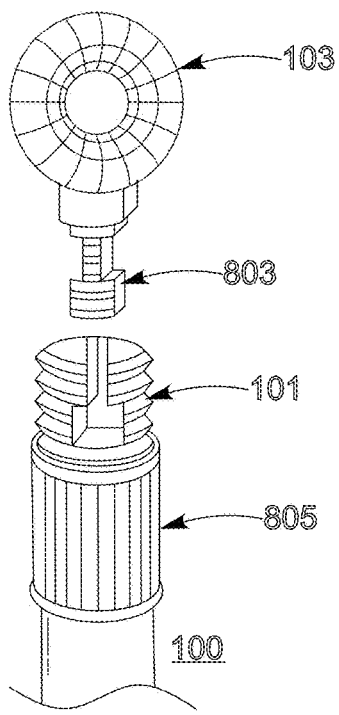
FIG. 15A shows an example of a removable head having a connector configured to couple with the handle of the acne extractor by inserting and rotating the threads of the connector into the handle of the acne extractor.
Figure 15B:
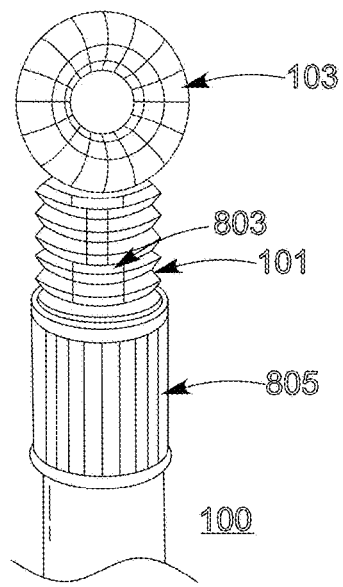
FIG. 15B shows an example of a removable head having a connector coupled to the handle of the acne extractor by inserting and rotating the threads of the connector into the handle of the acne extractor such that the connector sits flush with the handle of the acne extractor.
Figure 15C:
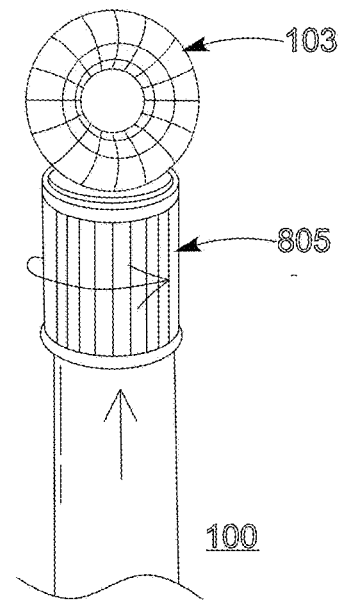
FIG. 15C shows an example of a removable head with a connector coupled to the handle of the acne extractor and a sleeve coupled to the connector by inserting and rotating the threads of the sleeve over the connector.

FIGS. 15A-15C are examples of how there may be additional features on the head 103 or handle 101 that utilize one or more mechanical systems to secure the head 103 to the handle 101. The mechanism to attach the head 103 to the handle 101 needs to be strong enough to prevent structural failure during extraction, and easy for the user to install and remove. FIG. 15A shows an example of a removable head 103 having a connector 803 configured to couple with the handle 101 of the acne extractor 100 by inserting and rotating the threads of the connector 803 into the handle 101 of the acne extractor 100. FIG. 15B shows an example of a removable head 103 having a connector 803 coupled to the handle 101 of the acne extractor 100 by inserting and rotating the threads of the connector 803 into the handle 101 of the acne extractor 100 such that the connector 803 sits flush with the handle 101 of the acne extractor 100. FIG. 15C shows an example of a removable head 103 with a connector 803 coupled to the handle 101 of the acne extractor 100 and a sleeve coupled to the connector by inserting and rotating the threads of the sleeve 805 over the connector 803.

Figures 16A, 16B, 16C:
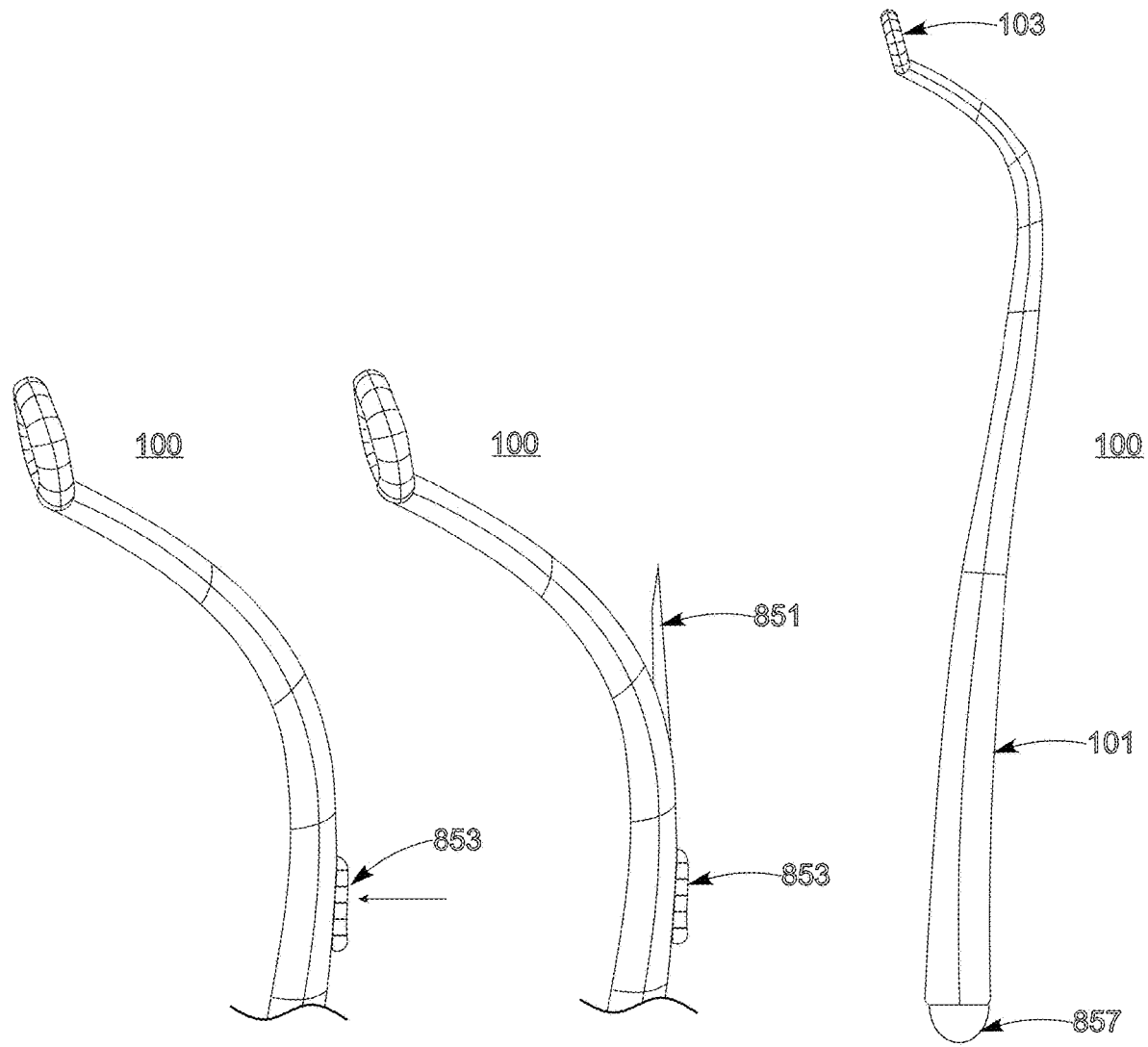
FIG. 16A shows an example of a sharp point enclosed inside the acne extractor.
FIG. 16B shows an example of a sharp point deployed from the extractor in response to pressing the button.
FIG. 16C shows an example of a removable pore-opening sharp tool configured to be stored inside the acne extractor.

FIGS. 16A-16B show examples of some embodiments, where there is a pore-opening appendage 851 attached to the acne extractor 100 that may pierce the pore of the acne to allow the application of less pressure to achieve the extraction. FIG. 16A shows an example of the pore-opening appendage 851 enclosed inside the acne extractor 100. FIG. 16B shows an example of the pore-opening appendage 851 deployed from the acne extractor 100 in response to pressing the button 853. Sometimes it is necessary to open the top of the acne with something sharp prior to extraction to reduce the amount of pressure needed to be applied by the acne extractor 100, so adding a pore-opening appendage 851 to the acne extractor 100 may protect the user from skin damage in certain circumstances if used correctly. To use the pore-opening appendage 851, the user may place the sharp tip of the pore-opening appendage 851 to the center of the acne and press lightly until only the outermost layer of the acne is pierced, which may allow the contents of the acne to be extracted with less force. This pore-opening appendage 851 may be sharp or blunt.

FIG. 16C shows an example of an acne extractor 100 wherein the proximate end is hollow and is configured to store a selectively removable pore-opening appendage 855. The sharp end of the removable pore-opening appendage 855 may be stored 859 inside the acne extractor 100 when not in use, and the user may grab the removable pore-opening appendage 855 at the end 857 to remove it from the acne extractor 100 and to use it to open pores. The removable pore-opening appendage 855 may be detachable from the handle 101 of the acne extractor 100 in a way where the user may hold it separately in their hand to open the pore prior to using the head 103 of the acne extractor 100 to extract the acne. The removable pore-opening appendage 855 may be detachable from the handle 101 of the acne extractor 100 in a way where the user may hold it separately in their hand to open the pore prior to using the head 103 of the acne extractor 100.

Figure 17A:
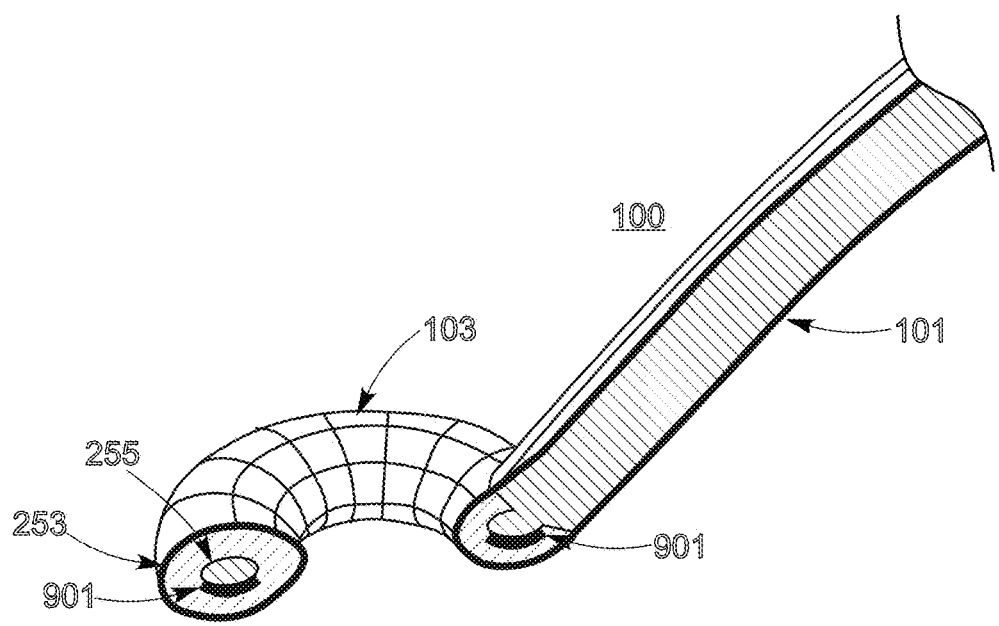
FIG. 17A shows an example of a cross-section of the acne extractor including a force sensor integrated into the head between the elastomeric material and the rigid handle.
Figures 17B, 17C:
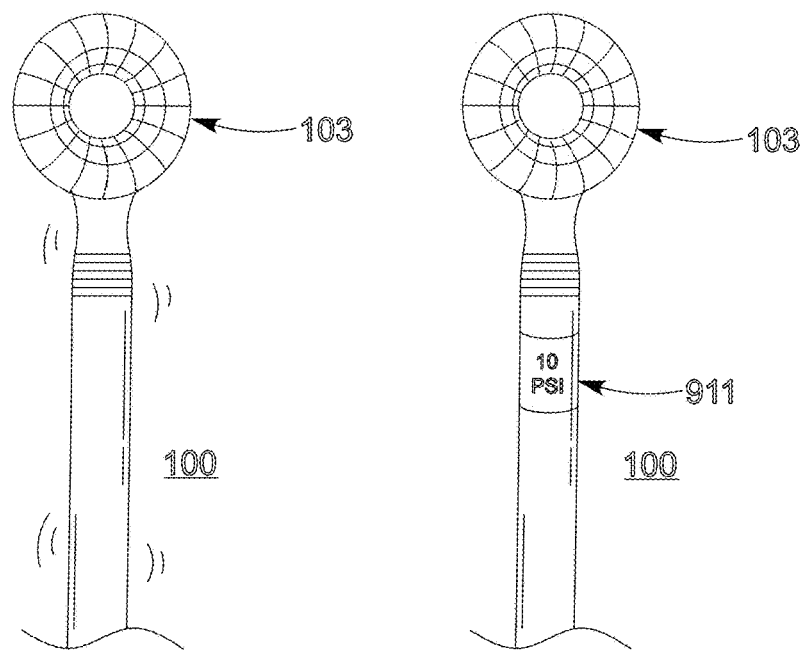
FIG. 17B shows an example of a vibration notification system configured to vibrate in response to a pressure threshold exceeding a defined limit.
FIG. 17C shows an example of a digital pressure gauge configured to display pressure data from the head of the acne extractor to notify a user when the pressure threshold has been exceeded.

FIGS. 17A-17C show examples of acne extractors 100 that have a built-in pressure-sensing system in the head 103 that notifies the user when a defined pressure has been reached while pressing the acne extractor 100 on the skin. There may be a sound or vibration that initiates when the maximum force is reached. There may be any combination of vibrations and/or sounds that alert the user when various forces are exerted on the skin. There can be other types of feedback to the user of the force they are exerting onto the skin with the extractor. This feature may help reduce the chance of inducing skin-trauma caused by exerting too much pressure on the skin that may lead to skin damage.

FIG. 17A shows an example of a cross-section of the acne extractor 100 including a pressure sensor 901 integrated into the head 103 between the elastomeric material 253 and the rigid material 255. A force sensor may be integrated into any part of the acne extractor's 100 head 103 or handle 101 and the processor used to define the pressure threshold and create notifications can also be located anywhere.

FIG. 17B shows an example of a vibration notification system configured to vibrate the acne extractor 100 in response to a pressure threshold of the head 103 exceeding a defined limit. FIG. 17C shows an example of a digital pressure gauge 911 configured to display pressure data from the head 103 of the acne extractor 100 to notify a user when the pressure threshold has been exceeded.

There may be a sensor that detects when the acne has begun to expel itself from the pore that is used to notify the user. This may be achieved using a sensor that detects when liquid is present. It can also be done using a pressure sensor 901, as shown in FIG. 17A, that detects a drop in pressure, which may indicate that the acne is expelling from the pore. The acne extractor 100 may also have a head 103 that has a pressure sensor 901 communicatively coupled to a speaker for emitting a sound in response to the pressure sensor detecting a pressure reading exceeding a pressure threshold.

The terminology used herein is for the purpose of describing particular embodiments only and is not intended to be limiting of the embodiments. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" is understood as within a range of normal tolerance in the art, for example within 2 standard deviations of the mean. "About" may be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

The many features and advantages of the disclosure are apparent from the detailed specification, and thus, it is intended by the appended claims to cover all such features and advantages of the disclosure which fall within the true spirit and scope of the disclosure. Further, since numerous modifications and variations will readily occur to those skilled in the art, it is not desired to limit the disclosure to the exact construction and operation illustrated and described, and accordingly, all suitable modifications and equivalents may be resorted to, falling within the scope of the disclosure In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The implementations set forth in the foregoing description do not represent all implementations consistent with the subject matter described herein. Instead, they are merely some examples consistent with aspects related to the described subject matter. Although a few variations have been described in detail herein, other modifications or additions are possible. In particular, further features and/or variations can be provided in addition to those set forth herein. For example, the implementations described above can be directed to various combinations and sub-combinations of the disclosed features and/or combinations and sub-combinations of one or more features further to those disclosed herein. In addition, the logic flows depicted in the accompanying figures and/or described herein do not necessarily require the particular order shown, or sequential order, to achieve desirable results. The scope of the following claims may include other implementations or embodiments.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

While the foregoing is directed to implementations of the present disclosure, other and further implementations of the disclosure may be devised without departing from the basic scope thereof, and the scope thereof is determined by the claims that follow.

What is claimed is:

1. An acne extractor for treating a skin irritation, the acne extractor comprising:
    a curved elongated handle having a distal end, the curved elongated handle including a button; and
    a head coupled to the distal end of the curved elongated handle, the head extending from the curved elongated handle at an angle and having a loop with an inner diameter, the inner diameter configured to encircle the skin irritation,
    wherein the loop is configured to apply an inward pressure to the skin irritation in response to pressing the loop against skin surrounding the skin irritation using the curved elongated handle, and
    wherein activating the button causes the inner diameter to decrease to create a pinching effect at the loop.

2. The acne extractor of claim 1, wherein the curved elongated handle and the head are formed from an elastomeric material and wherein the elastomeric material forming the curved elongated handle and the head are homogeneous.

3. The acne extractor of claim 1, wherein the head is selectively coupled to the curved elongated handle.

4. The acne extractor of claim 1, wherein the head includes a first portion with a first density and a second portion with a second density.

5. The acne extractor of claim 4, wherein the first portion is configured to flatten in response to being pressed against the skin thereby creating the inward pressure on the skin irritation.

6. The acne extractor of claim 1, wherein the head includes a first side and a second side, the first side including at least one of a plurality of recessions or a plurality of protrusions.

7. The acne extractor of claim 1, wherein the head has a circular shape.

8. An acne extractor for treating a skin irritation, the acne extractor comprising:
- a curved elongated handle having a distal end, the curved elongated handle including a button;
- a head coupled to the distal end of the curved elongated handle, the head extending from the curved elongated handle at an angle and having a loop with an inner diameter, the inner diameter configured to encircle the skin irritation, the head including a pressure sensor configured to generate pressure readings; and
- a speaker communicatively coupled to the pressure sensor, the speaker configured to emit a sound in response to the pressure sensor detecting a pressure reading exceeding a pressure threshold,
- wherein the loop is configured to apply an inward pressure to the skin irritation in response to pressing the loop against skin surrounding the skin irritation using the curved elongated handle.

9. The acne extractor of claim 8, wherein the curved elongated handle and the head are formed from an elastomeric material and wherein the elastomeric material forming the curved elongated handle and the head are homogeneous.

10. The acne extractor of claim 8, wherein the head is selectively coupled to the curved elongated handle.

11. The acne extractor of claim 8, wherein the head includes a first portion with a first density and a second portion with a second density.

12. The acne extractor of claim 11, wherein the first portion is configured to flatten in response to being pressed against the skin thereby creating the inward pressure on the skin irritation.

13. The acne extractor of claim 8, wherein the head includes a first side and a second side, the first side including at least one of a plurality of recessions or a plurality of protrusions.

14. The acne extractor of claim 8, wherein the head has a circular shape.

15. An acne extractor for treating a skin irritation, the acne extractor comprising:
- a curved elongated handle having a distal end, the curved elongated handle including a tightening knob; and
- a head coupled to the distal end of the curved elongated handle, the head extending from the curved elongated handle at an angle and having a loop with an inner diameter, the inner diameter configured to encircle the skin irritation,
- wherein the loop is configured to apply an inward pressure to the skin irritation in response to pressing the loop against skin surrounding the skin irritation using the curved elongated handle, and
- wherein the tightening knob is configured to adjust the angle of the head relative to the curved elongated handle.

16. The acne extractor of claim 15, wherein the curved elongated handle and the head are formed from an elastomeric material and wherein the elastomeric material forming the curved elongated handle and the head are homogeneous.

17. The acne extractor of claim 15, wherein the head is selectively coupled to the curved elongated handle.

18. The acne extractor of claim 15, wherein the head includes a first portion with a first density and a second portion with a second density.

19. The acne extractor of claim 18, wherein the first portion is configured to flatten in response to being pressed against the skin thereby creating the inward pressure on the skin irritation.

20. The acne extractor of claim 15, wherein the head includes a first side and a second side, the first side including at least one of a plurality of recessions or a plurality of protrusions.

* * * * *